(12) United States Patent
Kao et al.

(10) Patent No.: US 11,451,916 B2
(45) Date of Patent: Sep. 20, 2022

(54) SOUND ADJUSTMENT METHOD AND SOUND ADJUSTMENT DEVICE

(71) Applicant: Airoha Technology Corp., Hsinchu (TW)

(72) Inventors: Kuo-Wei Kao, Taipei (TW); Po-Jui Wu, Taipei (TW); Yu-Chieh Huang, Taipei (TW); Wei-Lin Chang, Taipei (TW); Kai-Yuan Hsiao, Taipei (TW); Cheng-Te Wang, Taipei (TW); I-Ting Lee, Taipei (TW); Kuo-Ping Yang, Taipei (TW)

(73) Assignee: AIROHA TECHNOLOGY CORP., Hsinchu (TW)

( * ) Notice: Subject to any disclaimer, the term of this patent is extended or adjusted under 35 U.S.C. 154(b) by 437 days.

(21) Appl. No.: 16/674,004

(22) Filed: Nov. 5, 2019

(65) Prior Publication Data

US 2021/0021947 A1 Jan. 21, 2021

(30) Foreign Application Priority Data

Jul. 18, 2019 (TW) ................................. 108125455

(51) Int. Cl.
| | |
|---|---|
| *H04S 1/00* | (2006.01) |
| *A61M 21/00* | (2006.01) |
| *G10L 19/018* | (2013.01) |
| *A61M 21/02* | (2006.01) |
| *H04R 5/04* | (2006.01) |
| *G10L 21/0364* | (2013.01) |

(52) U.S. Cl.
CPC ............ *H04S 1/007* (2013.01); *A61M 21/00* (2013.01); *G10L 19/018* (2013.01); *A61M 2021/0033* (2013.01); *H04S 2400/15* (2013.01)

(58) Field of Classification Search
None
See application file for complete search history.

(56) References Cited

U.S. PATENT DOCUMENTS

| | | | |
|---|---|---|---|
| 5,135,468 A | 8/1992 | Meissner | |
| 9,987,459 B2* | 6/2018 | Donnet | ................ A61M 21/00 |
| 2013/0010967 A1* | 1/2013 | Atwater | ................ H04S 1/007 |
| | | | 381/1 |
| 2013/0216055 A1* | 8/2013 | Wanca | ................ H03G 5/005 |
| | | | 381/61 |
| 2020/0330322 A1* | 10/2020 | Kang | ................ A61H 15/0078 |

* cited by examiner

*Primary Examiner* — Qin Zhu
(74) *Attorney, Agent, or Firm* — McClure, Qualey & Rodack, LLP

(57) ABSTRACT

A sound adjustment method is disclosed. The sound adjustment method includes the following the steps: receiving a sound adjustment command; receiving a right channel sound signal and a left channel sound signal; selecting a corresponding adjustment mode according to the sound adjustment command and processing the right channel sound signal and the left channel sound signal based on the adjustment mode to generate a right channel first sound signal and a left channel first sound signal, wherein different adjustment modes have different intensity adjustment levels; shifting the frequency of the right channel first sound signal by X Hz to generate a right channel second sound signal and shifting the frequency of the left channel first sound signal by Y Hz to generate a left channel second sound signal, wherein 0.5≤|X−Y|≤100; outputting the right channel second sound signal and the left channel second sound signal.

10 Claims, 3 Drawing Sheets

| adjustment modes | right channel first sound signal | left channel first sound signal | intensity adjustment levels |
|---|---|---|---|
| 1 | right channel sound signal | left channel sound signal | smaller ↕ larger |
| 2 | 90% of right channel sound signal +10% of left channel sound signal | 10% of right channel sound signal +90% of left channel sound signal | |
| 3 | 80% of right channel sound signal +20% of left channel sound signal | 20% of right channel sound signal +80% of left channel sound signal | |
| 4 | 70% of right channel sound signal +30% of left channel sound signal | 30% of right channel sound signal +70% of left channel sound signal | |
| 5 | 60% of right channel sound signal +40% of left channel sound signal | 40% of right channel sound signal +60% of left channel sound signal | |
| 6 | 50% of right channel sound signal +50% of left channel sound signal | 50% of right channel sound signal +50% of left channel sound signal | |

| adjustment modes | right channel first sound signal | left channel first sound signal | intensity adjustment levels |
|---|---|---|---|
| 1 | right channel sound signal | left channel sound signal | smaller ↕ larger |
| 2 | 90% of right channel sound signal +10% of left channel sound signal | 10% of right channel sound signal +90% of left channel sound signal | |
| 3 | 80% of right channel sound signal +20% of left channel sound signal | 20% of right channel sound signal +80% of left channel sound signal | |
| 4 | 70% of right channel sound signal +30% of left channel sound signal | 30% of right channel sound signal +70% of left channel sound signal | |
| 5 | 60% of right channel sound signal +40% of left channel sound signal | 40% of right channel sound signal +60% of left channel sound signal | |
| 6 | 50% of right channel sound signal +50% of left channel sound signal | 50% of right channel sound signal +50% of left channel sound signal | |

FIG.2

SOUND ADJUSTMENT METHOD AND SOUND ADJUSTMENT DEVICE

BACKGROUND OF THE INVENTION

1. Field of the Invention

The present invention relates to a sound adjustment method and a sound adjustment device; more particularly, the present invention relates to a sound adjustment method and a sound adjustment device for outputting sounds which can generate binaural beats by adjusting an inputted stereo sound.

2. Description of the Related Art

In 1839, the German psychologist H. W. Dove first identified the "Binaural Beats Effect", which means that when a person's ears respectively hear similar sounds which have different frequencies, the waves of the sounds are integrated in the person's brain to produce a third sound (i.e., a binaural beat) which has a frequency equal to the difference in frequency between the sounds. For example, if a left ear and a right ear respectively and simultaneously hear a sound whose frequency is 124 Hz and another sound whose frequency is 114 Hz, a brain will produce a binaural beat which has a frequency of 10 Hz.

According to research in brain science, the human brain can generate different types of brain waves when humans experience different emotions or mental states. Common types of brain waves include delta waves (having a frequency of about 0.5-3 Hz), theta waves (having a frequency of about 3-8 Hz), alpha waves (having a frequency of about 8-12 Hz), beta waves (having a frequency of about 12-38 Hz) and gamma waves (having a frequency of about 38-100 Hz). At present, many studies have indicated that if the frequency of binaural beats is located within a frequency range of a specific brain wave, the binaural beats can induce the human brain to generate a corresponding brain wave, as described in U.S. Pat. No. 5,135,468, which discloses a technique which involves application of these studies.

Therefore, when a person listens to music, if sounds which can generate binaural beats can be generated by adjusting the sound output, the generated sounds will induce the listener's brain to generate a brain wave which has a specific frequency which in turn will adjust the listener's physical and mental states. Although the prior art has disclosed how to create differences in frequency between sounds to generate binaural beats, the intensity of the binaural beats cannot be adjusted by a user.

SUMMARY OF THE INVENTION

It is a primary object of the present invention to provide a sound adjustment method for adjusting and outputting sounds which can generate binaural beats according to a user's need.

It is another primary object of the present invention to provide a sound adjustment device for performing the abovementioned method.

To achieve the abovementioned objects, the sound adjustment method comprises the following steps: receiving a sound adjustment command; receiving a right channel sound signal and a left channel sound signal which is different from the right channel sound signal; selecting a corresponding adjustment mode according to the sound adjustment command and processing the right channel sound signal and the left channel sound signal based on the adjustment mode to generate a right channel first sound signal and a left channel first sound signal, wherein different adjustment modes have different intensity adjustment levels; when the adjustment mode has a greater intensity adjustment level, the right channel first sound signal is more similar to the left channel first sound signal; when the adjustment mode has a smaller intensity adjustment level, the right channel first sound signal is less similar to the left channel first sound signal; shifting the frequency of the right channel first sound signal by X Hz to generate a right channel second sound signal and shifting the frequency of the left channel first sound signal by Y Hz to generate a left channel second sound signal, wherein $0.5 \leq |X-Y| \leq 100$; outputting the right channel second sound signal and the left channel second sound signal.

The sound adjustment device of the present invention comprises a command receiving end, a sound signal input end, a signal processing module, a frequency adjustment module and a sound signal output end. The command receiving end receives a sound adjustment command. The sound signal input end receives a right channel sound signal and a left channel sound signal which is different from the right channel sound signal. The signal processing module is electrically connected to the command receiving end and the sound signal input end. The signal processing module selects a corresponding adjustment mode according to the sound adjustment command and then processes the right channel sound signal and the left channel sound signal based on the adjustment mode to generate a right channel first sound signal and a left channel first sound signal, wherein different adjustment modes have different intensity adjustment levels; when the adjustment mode has a greater intensity adjustment level, the right channel first sound signal is more similar to the left channel first sound signal, and when the adjustment mode has a smaller intensity adjustment level, the right channel first sound signal is less similar to the left channel first sound signal. The frequency adjustment module shifts the frequency of the right channel first sound signal by X Hz to generate a right channel second sound signal and shifts the frequency of the left channel first sound signal by Y Hz to generate a left channel second sound signal, wherein $0.5 \leq |X-Y| \leq 100$. The sound signal output end is electrically connected to the frequency adjustment module. The sound signal output end outputs the right channel second sound signal and the left channel second sound signal.

Other objects, advantages, and novel features of the invention will become more apparent from the following detailed description when taken in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views:

FIG. 2 illustrates a schematic drawing showing a right channel sound signal and a left channel sound signal respectively processed into different right channel first sound signals and left channel first sound signals according to different adjustment modes.

DETAILED DESCRIPTION OF THE PREFERRED EMBODIMENT

Figure 1:
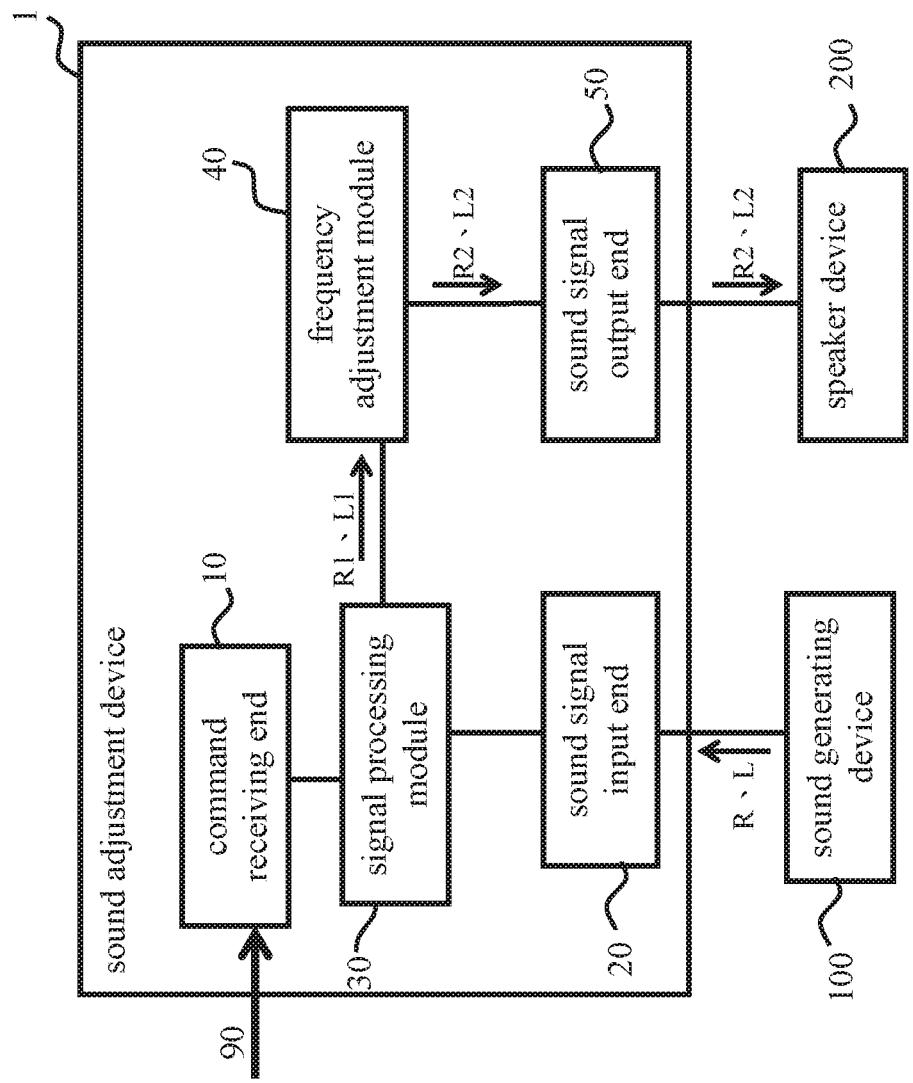
FIG. 1 illustrates a device structural drawing of a sound adjustment device according to one embodiment of the present invention.

Please refer to FIG. 1 and FIG. 2. FIG. 1 illustrates a device structural drawing of a sound adjustment device according to one embodiment of the present invention; FIG. 2 illustrates a schematic drawing showing a right channel sound signal and a left channel sound signal respectively processed into different right channel first sound signals and left channel first sound signals according to different adjustment modes.

As shown in FIG. 1, in one embodiment of the present invention, the sound adjustment device 1 of the present invention is used for adjusting a right channel sound signal R and a left channel sound signal L inputted by a sound generating device 100 and then outputting to a speaker device 200 a right channel second sound signal R2 generated by adjustment of the right channel sound signal R and a left channel second sound signal L2 generated by adjustment of the left channel sound signal L, In a specific embodiment of the present invention, the sound generating device 100 may be a device that generates a sound signal, such as an audio device, a television, or a mobile phone, wherein the source of the generated sound signals may include but is not limited to the Internet, storage media or a microphone (not shown in figures); the speaker device 200 may be a headphone or a speaker, but the present invention is not limited to the devices listed above. In addition, in a preferred embodiment, the sound adjustment device 1 may be a microprocessor chip disposed in the sound generating device 100 and may communicate with the speaker device 200 in a wired or wireless manner. However, the invention is not limited thereto. In other embodiments, the sound adjustment device 1 may also be disposed in the speaker device 200 to communicate with the sound generating device 100 in a wired or wireless manner.

As shown in FIG. 1, in an embodiment of the present invention, the sound adjustment device 1 includes a command receiving end 10, a sound signal input end 20, a signal processing module 30, a frequency adjustment module 40 and a sound signal output end 50.

In an embodiment of the present invention, the command receiving end 10 is used for receiving a sound adjustment command 90. In a specific embodiment of the present invention, the sound adjustment command 90 is inputted by a user operating an input interface (not shown in figures) disposed on the sound adjustment device 1. For example, the sound adjustment device 1 may have a screen (not shown in figures) which can display a virtual button. The user can input the sound adjustment command 90 by clicking the virtual button, but the input interface of the present invention is not limited to the virtual button. The input interface may also be a physical button or other user interfaces, and the sound adjustment command 90 mentioned in the present invention is also not limited to being generated by a user's input.

In an embodiment of the present invention, the sound signal input end 20 communicates with the sound generating device 100 to receive and obtain a right channel sound signal R and a left channel sound signal L generated by the sound generating device 100, wherein the right channel sound signal R is different from the left channel sound signal L.

In an embodiment of the present invention, the signal processing module 30 is electrically connected to the command receiving end 10 and the sound signal input end 20. The signal processing module 30 is used for selecting a corresponding adjustment mode from a plurality of adjustment modes according to the sound adjustment command 90 and processing the right channel sound signal R and the left channel sound signal L based on the adjustment mode to generate a right channel first sound signal R1 and a left channel first sound signal L1, wherein the different adjustment modes have different intensity adjustment levels. For example, above the input interface may be displayed a plurality of virtual buttons, and a user can input different sound adjustment commands by clicking the different virtual buttons, wherein the different sound adjustment commands respectively correspond to the different adjustment modes. The signal processing module 30 can select one of the adjustment modes to produce sound signals according to the sound adjustment command 90 received by the command receiving end 10.

As shown in FIG. 2, in an embodiment of the present invention, the sound adjustment device 1 contains six built-in adjustment modes from mode 1 to mode 6, and the intensity adjustment levels of mode 1 to mode 6 are ordered from small to large. When the intensity adjustment level is larger, the retained proportion of the original signal is smaller. Conversely, when the intensity adjustment level is smaller, the retained proportion of the original signal is larger. In an embodiment of the present invention, the right channel first sound signal R1 is generated based on the formula R1=mL+nR, wherein n+M=1, $0.5 \le n \le 1$ and $0 \le m \le 0.5$, and wherein R1 represents the right channel first sound signal R1, L represents the left channel sound signal L, and R represents the right channel sound signal R. The left channel first sound signal L1 is generated based on the formula L1=nL+mR, wherein n+m=1, $0.5 \le n \le 1$ and $0 \le m \le 0.5$, and wherein L1 represents the left channel first sound signal L1, L represents the left channel sound signal L, and R represents the right channel sound signal R.

As shown in FIG. 2, in the mode 1, the above parameter n=1 and the above parameter m=0. Thus, when the mode 1 is selected, the right channel first sound signal R1 is equal to the right channel sound signal R, and the left channel first sound signal L1 is equal to the left channel sound signal L. In the mode 2, the above parameter n=0.9 and the above parameter m=0.1. Thus, when the mode 2 is selected, the right channel first sound signal R consists of ninety percent of the right channel sound signal R and ten percent of the left channel sound signal L, and the left channel first sound signal L1 consists of ten percent of the right channel sound signal R and ninety percent of the left channel sound signal L. In the mode 3, the above parameter n=0.8 and the above parameter m=0.2. Thus, when the mode 3 is selected, the right channel first sound signal R1 consists of eighty percent of the right channel sound signal R and twenty percent of the left channel sound signal L, and the left channel first sound signal L1 consists of twenty percent of the right channel sound signal R and eighty percent of the left channel sound signal L. In the mode 4, the above parameter n=0.7 and the above parameter m=0.3. Thus, when the mode 4 is selected, the right channel first sound signal R1 consists of seventy percent of the right channel sound signal R and thirty percent of the left channel sound signal L, and the left channel first sound signal L1 consists of thirty percent of the right channel sound signal R and seventy percent of the left channel sound signal L. In the mode 5, the above parameter n=0.6 and the above parameter m=0.4. Thus, when the mode 5 is selected, the right channel first sound signal R1 consists of sixty percent of the right channel sound signal R and forty percent of the left channel sound signal L, and the left channel first sound signal L1 consists of forty percent of the right channel sound signal R and sixty percent of the left channel sound signal L. In the mode 6, the above parameter n=0.5 and the above parameter m=0.5. Thus, when the mode 6 is selected, the right channel first sound signal R1 consists of fifty percent of the right channel sound signal R and fifty percent of the left channel sound signal L, and the left channel first sound signal L1 consists of fifty percent of the right channel sound signal R and fifty percent of the left channel sound signal L.

According to the abovementioned description, a larger intensity adjustment level selected with the signal processing module 30 corresponds to greater similarity between the right channel first sound signal R1 and the left channel first sound signal L1, and a smaller intensity adjustment level selected with the signal processing module 30 corresponds to less similarity between the right channel first sound signal R1 and the left channel first sound signal L1. When the adjustment mode has the largest intensity adjustment level (i.e., the mode 6), the right channel first sound signal R1 is an equal mixture of the right channel sound signal R and the left channel sound signal L, and the left channel first sound signal L1 is also an equal mixture of the right channel sound signal R and the left channel sound signal L. Therefore, in this mode, the right channel first sound signal R1 and the left channel first sound signal L1 are the same. When the adjustment mode has a smallest intensity adjustment level (i.e., the mode 1), the right channel first sound signal R1 is equal to the right channel sound signal R, and the left channel first sound signal L1 is equal to the left channel sound signal L. Therefore, in this mode, the difference between the right channel first sound signal R1 and the left channel first sound signal L1 is the largest.

In an embodiment of the present invention, the frequency adjustment module 40 is electrically connected to the signal processing module 30. The frequency adjustment module 40 is used for shifting the frequency of the right channel first sound signal R1 by X Hz to generate a right channel second sound signal R2 and for shifting the frequency of the left channel first sound signal L1 by Y Hz to generate a left channel second sound signal L2, wherein 0.5≤|X−Y|≤100. In a specific embodiment of the present invention, the frequency adjustment module 40 shifts the frequency of the right channel first sound signal R1 by 5 Hz (i.e., an increase in frequency of 5 Hz, X=5) to generate the right channel second sound signal R2 and shifts the frequency of the left channel first sound signal L1 by −5 Hz (i.e., a decrease in frequency of 5 Hz, Y=−5) to generate the left channel second sound signal L2, but the present invention is not limited to this adjustment. Therefore, the similar sound contents of the right channel second sound signal R2 and the left channel second sound signal L2 have a difference in frequency of 10 Hz after the right channel first sound signal R1 and the left channel first sound signal L1 are processed by shifting the frequencies.

For example, when the signal processing module 30 selects the mode 6 as the adjustment mode according to the sound adjustment command 90 inputted by a user, the sound contents of the right channel first sound signal R1 and the left channel first sound signal L1 generated by processing the right channel sound signal R and the left channel sound signal L based on the mode 6 are exactly the same. After the right channel first sound signal R1 and the left channel first sound signal L1 which have the same sound contents are processed by the abovementioned shifts in frequency, sounds which can generate binaural beats with the largest binaural beats effect will be generated.

In an embodiment of the present invention, the sound signal output end 50 is electrically connected to the frequency adjustment module 40 and communicates with the speaker device 200 in a wired or wireless manner. The sound signal output end 50 is used for outputting the right channel second sound signal R2 and the left channel second sound signal L2.

Please note that the signal processing module 30 and the frequency adjustment module 40 can be accomplished by hardware devices, software programs, firmware or combinations thereof, and that they can also be configured in the form of circuit loops or other suitable formats; further, each of the modules can be configured either in an independent form or in a combined form. In one preferred embodiment, each of the modules is a software program stored in a storage unit (not shown in figures) of the controller, and a processing unit (not shown in figures) of the controller will execute each module to achieve the purpose of the present invention. Moreover, the embodiment disclosed herein only describes a preferred embodiment of the present invention. To avoid redundant description, not all possible variations and combinations are described in detail in this specification. However, those skilled, in the art will understand that the above modules or components are not all necessary parts, and that in order to implement the present invention, other more detailed known modules or components might also be included. It is possible that each module or component can be omitted or modified depending on different requirements, and it is also possible that other modules or components might be disposed between any two modules.

Figure 3:
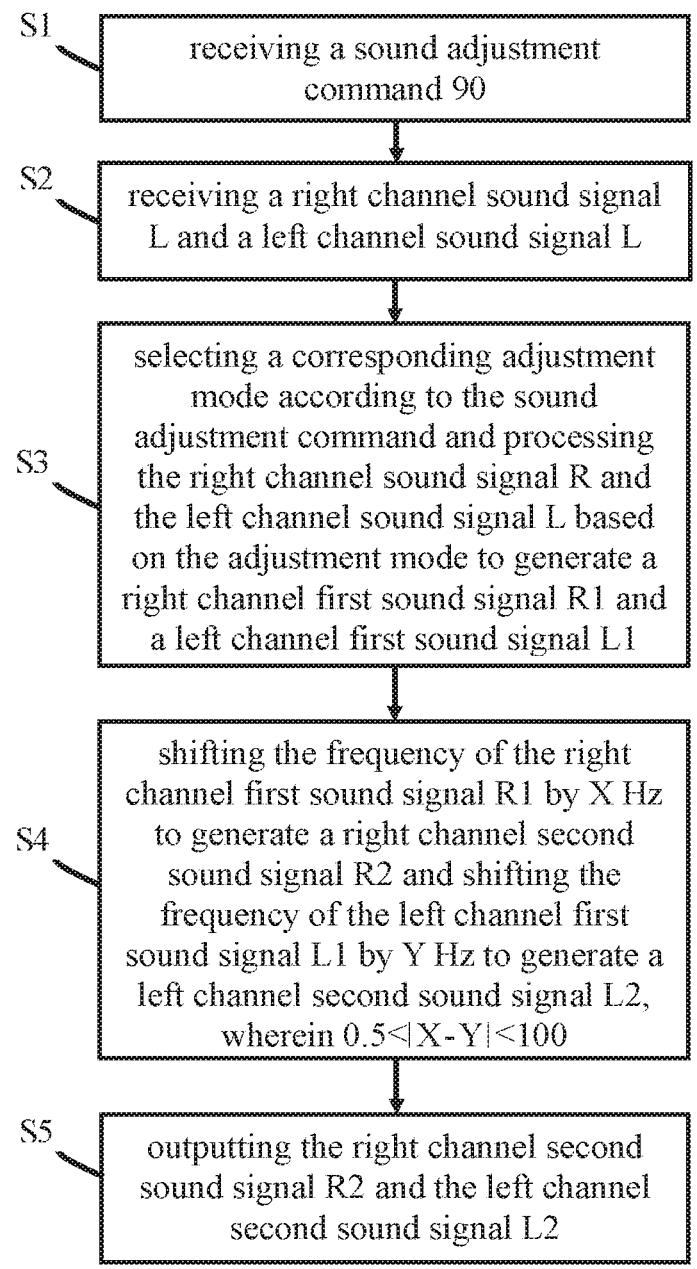
FIG. 3 illustrates a flowchart of a sound adjustment method according to one embodiment of the present invention.

Please refer to FIG. 1 to FIG. 3 together. FIG. 3 illustrates a flowchart of a sound adjustment method according to one embodiment of the present invention. The steps disclosed in FIG. 3 will be explained by referring to FIG. 1 and FIG. 2 in the following paragraphs. Please note that the sound adjustment device 1 as shown in FIG. 1 is used as an example to explain the sound adjustment method of the present invention; however, the sound adjustment method of the present invention is not limited to application to a device having the same structure as the abovementioned sound adjustment device 1 only.

First, the method performs step S1: receiving a sound adjustment command 90.

In an embodiment of the present invention, a user can input a sound adjustment command 90 to the sound adjustment device 1 by operating the input interface of the sound adjustment device 1. The command receiving end 10 receives the sound adjustment command 90.

Performing step S2: receiving a right channel sound signal L and a left channel sound signal L.

In an embodiment of the present invention, the sound signal input end 20 communicates with the sound generating device 100 in a wired or wireless manner to receive and obtain a right channel sound signal R and a left channel sound signal L. In general, a right channel sound signal and a left channel sound signal of a stereo sound are not completely the same, so the right channel sound signal R and the left channel sound signal L are different.

Performing step S3: selecting a corresponding adjustment mode according to the sound adjustment command and processing the right channel sound signal R and the left channel sound signal L based on the adjustment mode to generate a right channel first sound signal R1 and a left channel first sound signal L1.

When the command receiving end 10 receives the sound adjustment command 90, the signal processing module 30 can select a corresponding adjustment mode from a plurality of adjustment modes according to the sound adjustment command 90 and process the right channel sound signal R and the left channel sound signal L based on the adjustment mode to generate a right channel first sound signal R1 and a left channel first sound signal L1 after the sound signal input end 20 acquires the right channel sound signal R and the left channel sound signal L. In a specific embodiment, the sound adjustment device 1 contains six built-in adjustment modes from mode 1 to mode 6 as shown FIG. 2, and the different adjustment modes respectively have different intensity adjustment levels. The details of how the signal processing module 30 produces and generates the different right channel first sound signal R1 and left channel first sound signal L based on different adjustment modes are described above, so no further description of the details will be included here.

Performing step S4: shifting the frequency of the right channel first sound signal R1 by X Hz to generate a right channel second sound signal R2 and shifting the frequency of the left channel first sound signal L1 by Y Hz to generate a left channel second sound signal L2, wherein $0.5 \leq |X-Y| \leq 100$.

In an embodiment of the present invention, after the right channel first sound signal R1 and left channel first sound signal L1 are obtained, the frequency adjustment module 40 can shift the frequency of the right channel first sound signal R1 by X Hz to generate a right channel second sound signal R2 and shift the frequency of the left channel first sound signal L1 by Y Hz to generate a left channel second sound signal L2, wherein $0.5 \leq |X-Y| \leq 100$. For example, the frequency adjustment module 40 can shift only the frequency of the right channel first sound signal R1 by 10 Hz (an increase in frequency of 10 Hz), i.e., X=10, Y=0; the frequency adjustment module 40 can shift only the frequency of the left channel first sound signal L1 by 10 Hz (an increase in frequency of 10 Hz), i.e., X=0, Y=10; the frequency adjustment module 40 can also shift the frequency of the right channel first sound signal R1 by 5 Hz (an increase in frequency of 5 Hz) and shift the frequency of the left channel first sound signal L1 by −5 Hz (a decrease in frequency of 5 Hz) synchronously, i.e., X=5, Y=−5, where $|X|=|Y|$. Therefore, after the right channel first sound signal R1 and the left channel first sound signal L1 are obtained, the frequency adjustment module 40 can synchronously or alternatingly adjust the frequencies of the right channel first sound signal R1 and the left channel first sound signal L1.

Finally, performing step S5: outputting the right channel second sound signal R2 and the left channel second sound signal L2.

After the step S4 is performed, the sound signal output end 50 can output the right channel second sound signal R2 and the left channel second sound signal L2 to the speaker device 200 such that the right channel second sound signal R2 and the left channel second sound signal L2 are played by the speaker device 200.

It is noted that the sequence of the steps of the sound adjustment method of the present invention is not limited to the above description.

According to the abovementioned description, the sound adjustment method of the present invention can adjust and output different sounds that can generate binaural beats with different intensity effects according to the sound adjustment command 90 inputted by the user.

Please note that the abovementioned embodiment only describes a preferred embodiment of the present invention. To avoid redundant description, not all possible variations and combinations are described in detail in this specification. However, those skilled in the art will understand that the above modules or components are not all necessary parts, and that in order to implement the present invention, other more detailed known modules or components might also be included. It is possible that each module or component can be omitted or modified depending on different requirements, and it is also possible that other modules or components might be disposed between any two modules.

Although the present invention has been explained in relation to its preferred embodiments, it is to be understood that many other possible modifications and variations can be made without departing from the spirit and scope of the invention as hereinafter claimed.

What is claimed is:

1. A sound adjustment method, comprising the following steps:

receiving a sound adjustment command;

receiving a right channel sound signal and a left channel sound signal which is different from the right channel sound signal;

selecting a corresponding adjustment mode according to the sound adjustment command and processing the right channel sound signal and the left channel sound signal based on the adjustment mode to generate a right channel first sound signal and a left channel first sound signal, wherein different adjustment modes have different intensity adjustment levels; when the adjustment mode has a greater intensity adjustment level, the right channel first sound signal is more similar to the left channel first sound signal; when the adjustment mode has a smaller intensity adjustment level, the right channel first sound signal is less similar to the left channel first sound signal;

when the adjustment mode has the largest intensity adjustment level, the right channel first sound signal is an equal mixture of the right channel sound signal and the left channel sound signal and the left channel first sound signal is also an equal mixture of the right channel sound signal and the left channel sound signal;

shifting the frequency of the right channel first sound signal by X Hz to generate a right channel second sound signal and shifting the frequency of the left channel first sound signal by Y Hz to generate a left channel second sound signal, wherein $0.5 \leq |X-Y| \leq 100$; and outputting the right channel second sound signal and the left channel second sound signal.

2. The sound adjustment method as claimed in claim 1, wherein when the adjustment mode has the smallest intensity adjustment level, the right channel first sound signal is equal to the right channel sound signal and the left channel first sound signal is equal to the left channel sound signal.

3. The sound adjustment method as claimed in claim 1, wherein $|X|=|Y|$.

4. The sound adjustment method as claimed in claim 1, wherein X=0 and Y≠0.

5. The sound adjustment method as claimed in claim 1, wherein X≠0 and Y=0.

6. A sound adjustment device, comprising:

a command receiving end, which receives a sound adjustment command;

a sound signal input end, which receives a right channel sound signal and a left channel sound signal which is different from the right channel sound signal;

a signal processing module, which is electrically connected to the command receiving end and the sound signal input end and selects a corresponding adjustment mode according to the sound adjustment command and processes the right channel sound signal and the left channel sound signal based on the adjustment mode to generate a right channel first sound signal and a left channel first sound signal, wherein different adjustment modes have different intensity adjustment levels; when the adjustment mode has a greater intensity adjustment level, the right channel first sound signal is more similar to the left channel first sound signal; when the adjustment mode has a smaller intensity adjustment level, the right channel first sound signal is less similar to the left channel first sound signal; when the adjustment mode has the largest intensity adjustment level, the right channel first sound signal is an equal mixture of the right channel sound signal and the left channel sound signal and the left channel first sound signal is also an equal mixture of the right channel sound signal and the left channel sound signal;

a frequency adjustment module, which shifts the frequency of the right channel first sound signal by X Hz to generate a right channel second sound signal and shifts the frequency of the left channel first sound signal by Y Hz to generate a left channel second sound signal, wherein $0.5 \leq |X-Y| \leq 100$; and a sound signal output end, which is electrically connected to the frequency adjustment module and outputs the right channel second sound signal and the left channel second sound signal.

7. The sound adjustment device as claimed in claim 6, wherein when the adjustment mode has the smallest intensity adjustment level, the right channel first sound signal is equal to the right channel sound signal and the left channel first sound signal is equal to the left channel sound signal.

8. The sound adjustment device as claimed in claim 6, wherein $|X|=|Y|$.

9. The sound adjustment device as claimed in claim 6, wherein $X=0$ and $Y \neq 0$.

10. The sound adjustment device as claimed in claim 6, wherein $X \neq 0$ and $Y=0$.

* * * * *